US008436152B2

(12) United States Patent
Brinkman et al.

(10) Patent No.: US 8,436,152 B2
(45) Date of Patent: May 7, 2013

(54) METHODS FOR PURIFICATION OF ALPHA-1-ANTITRYPSIN AND APOLIPOPROTEIN A-1

(75) Inventors: Nathan Brinkman, Herscher, IL (US); Douglas Bigler, Kankaee, IL (US); Reinhard Bolli, Gümligen (CH); Vreni Foertsch, Winznau (CH)

(73) Assignee: CSL Behring GmbH, Marburg (DE)

( * ) Notice: Subject to any disclaimer, the term of this patent is extended or adjusted under 35 U.S.C. 154(b) by 156 days.

(21) Appl. No.: 12/673,723

(22) PCT Filed: Aug. 15, 2008

(86) PCT No.: PCT/US2008/009745
§ 371 (c)(1),
(2), (4) Date: Dec. 20, 2010

(87) PCT Pub. No.: WO2009/025754
PCT Pub. Date: Feb. 26, 2009

(65) Prior Publication Data
US 2011/0087008 A1 Apr. 14, 2011

Related U.S. Application Data

(60) Provisional application No. 60/935,527, filed on Aug. 17, 2007.

(51) Int. Cl.
*C07K 1/30* (2006.01)
(52) U.S. Cl.
USPC .......................................... 530/424; 530/380
(58) Field of Classification Search .................. None
See application file for complete search history.

(56) References Cited

U.S. PATENT DOCUMENTS
2004/0124143 A1 7/2004 Kee et al.

FOREIGN PATENT DOCUMENTS
| WO | WO 00/17227 | 3/2000 |
| WO | WO 2006/023831 A2 | 3/2006 |
| WO | WO 2007/062270 A2 | 5/2007 |
| WO | WO 2007/063129 A2 | 6/2007 |

OTHER PUBLICATIONS

Lerch et al. "Isolation and properties of apolipoprotein A for therapeutic use" Protide Biol. Fluids 36, 409-416 (1989).*
International Search Report PCT/US2008/009745 dated Mar. 10, 2009.
E. J. Cohn et al., "A System for the Separation of the Components of Human Blood: Quantitative Procedures for the Separation of the Protein Components of Human Plasma", Journal of the American Chemical Society 1950, vol. 72, No. 1. 1950, pp. 465-474.
S.T. Agnese et al., "Evaluation of Four Reagents for Delipidation of Serum", Clinical Biochemistry, Elsevier Inc. US, CA; vol. 16, No. 2, Apr. 1, 1983, pp. 98-100.
Charles B. Glaser et al., "The Isolation of Alpha-1-Protease Inhibitor by a Unique Procedure Designed for Industrial Application" Analytical Biochemistry, 124, (1982), pp. 364-371.
John G. Raynes et al., "Purification of Serum Amyloid A and Other High Density Apoliproteins by Hydrophobic Interaction Chromatography", Analytical Biochemistry, 173, pp. 116-124, (1988).
Sándor Oláh et al., "Hydrophobic interaction chromatography of human serum α1-antitrypsin and α1-acid glycoprotein", Journal of Chromatography B, 744 (2000) 73-79.
Kathrin Fetz et al., "Purification and partial characterization of feline α1-proteinase inhibitor (fα1-PI) and development and validation of a radioimmunoassay for the measurement of fα-PI in serum", Biochimie 86 (2004), pp. 67-75.
Manuel C. Peitsch et al., "A Purification Method for Apoliproprotein A-I and A-II", Analytical Biochemistry 178, 301-305 (1989).
David T. Vallance et al., "Precipitation procedures used to isolate high density lipoprotein with particular reference to effects on apo A-I-only particles and lipoprotein(a)", Clinica Chimica Acta 229 (1994) 77-85.
Sharon X. Chen et al., "Chromatographic purification of human α1 proteinase inhibitor from dissolved Cohn fraction IV-1 paste", Journal of Chromatography A, 800 (1998) 207-218.

* cited by examiner

*Primary Examiner* — Nashaat Nashed
(74) *Attorney, Agent, or Firm* — Foley & Lardner LLP

(57) ABSTRACT

This invention relates to protein separation and purification methods for both alpha-1-antitrypsin (AAT, also known as alpha-1 proteinase inhibitor, API, and $A_1$-PI) and Apolipoprotein A-I (ApoA-I) from, for example, a fraction of human blood plasma. In certain embodiments, the invention provides methods for separating AAT from ApoA-I at the initial stage of purification, so that the same starting material can be used as a source for both proteins. The methods further pertain to providing compositions of AAT and of ApoA-I suitable for pharmaceutical use and are suitable for large-scale purification.

13 Claims, 1 Drawing Sheet

Flow diagram illustrating an embodiment of the separation of ApoA-I and AAT as described in detail in Example 2
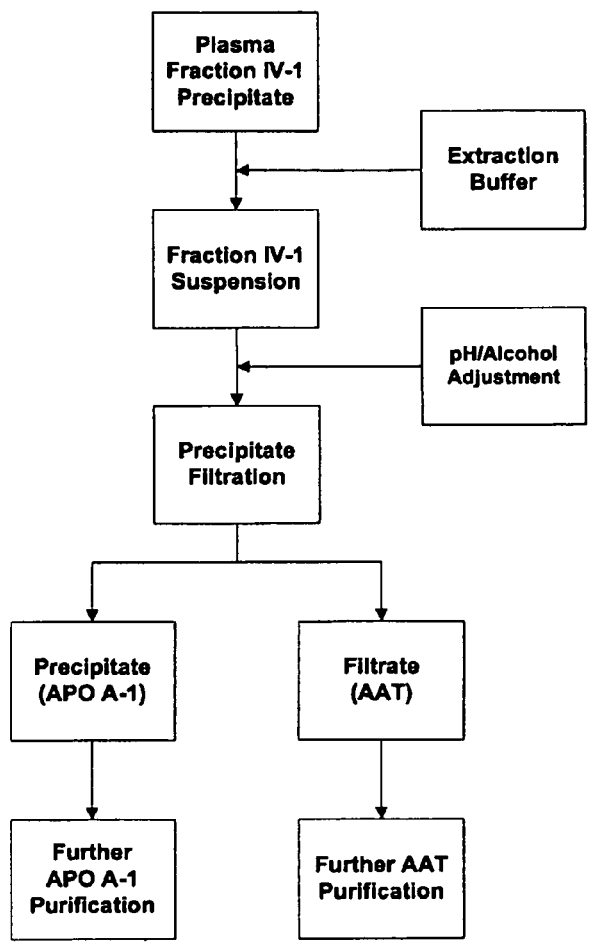

US 8,436,152 B2

METHODS FOR PURIFICATION OF ALPHA-1-ANTITRYPSIN AND APOLIPOPROTEIN A-1

CROSS REFERENCE TO RELATED APPLICATIONS

This application claims the benefit of priority of U.S. Provisional Application No. 60/935,527, which was filed Aug. 17, 2007 and is incorporated herein by reference in its entirety.

FIELD OF THE INVENTION

The invention relates to protein separation and purification methods for both alpha-1-antitrypsin (AAT, also known as alpha-1 proteinase inhibitor, API, and $A_1$-PI) and Apolipoprotein A-I (ApoA-I) from, for example, a fraction of human blood plasma. In certain embodiments, the invention provides methods for separating AAT from ApoA-I at the initial stage of purification, so that the same starting material can be used as a source for both proteins. The methods further pertain to providing compositions of AAT and of ApoA-I suitable for pharmaceutical use and are suitable for large-scale purification.

BACKGROUND OF THE INVENTION

Many protein-based biopharmaceuticals are isolated from human plasma. The limited supply of the raw material human plasma, which relies partially on voluntary blood donation, combined with the generally low concentration, high fragility, and limited yield in purification of blood plasma proteins make the manufacturing of this class of medicaments difficult and expensive. There is thus a need to improve the efficiency of methods of purification of blood plasma proteins, so that as many medically relevant proteins as possible can be isolated from the same sample of human plasma in the highest yield achievable.

Protein separation and purification processes for human plasma proteins present unique challenges due to the variety of proteins, the varying nature of possible contaminants and/or impurities associated with each protein preparation, and the large quantity of protein usually needed for the production of biopharmaceuticals. Purification technologies generally involve a series of purification steps with the objective of isolating a single protein target.

Alpha-1-antitrypsin (AAT) and Apolipoprotein A-I (ApoA-I) are examples of human plasma proteins that can be manufactured into biopharmaceuticals. Methods to purify these proteins using dedicated purification processes have been described. For example PCT Publication No. WO04060528 describes a purification process for AAT and U.S. Pat. No. 5,089,602 describes the purification of ApoA-I, each process starting from human blood plasma fractions and each leading to a single protein product.

We have now developed methods allowing the purification of AAT and ApoA-I starting from the same fraction of human plasma. These methods are suitable for large-scale purification, thus providing the basis for industrially applicable manufacturing processes. The invention provides methods for separating AAT from ApoA-I at the initial stages of purification, so that the same starting material can be used as a starting material to purify both proteins, and methods to produce pharmaceutical-grade AAT and ApoA-I after said separation.

ApoA-I is a 28 kDa major protein constituent of high-density lipoprotein (HDL) and plays a key role in the reverse transport of cholesterol from the periphery to the liver for excretion or recycling.

ApoA-I particularly in reconstituted HDL-like particles has long been described as having therapeutic potential. Only recently a study was published which underscores this potential (JAMA (2007); vol. 297, p. 1675-1682).

A variety of purification techniques for ApoA-I have been developed.

One of the most common ways to purify ApoA1 on a small scale is to use ultracentrifugation in order to isolate HDL followed by a separation of ApoA-I from the HDL-particle. There are several different ways to purify ApoA-I from HDL, including solvent extraction. Ultracentrifugation is a very time-consuming method, and it is not suitable for large-scale isolation.

Methods using plasma as starting material that do not include ultracentrifugation have also been described, for example, chromatographic purification (Ross S. E. et al., Rapid chromatographic purification of apolipoproteins A-I and A-II from human plasma, Analytical Biochemistry 149, p. 166-168 (1985)) and purification using gel-filtration HPLC (Tricerri A. et al., A rapid and efficient procedure for the purification of human apolipoprotein A-I using gel-filtration HPLC, IJBC, 1, p. 159-166 (1994)). Other methods that use fractions from cold ethanol fractionation of human plasma as the starting material have also been published (Peitsch et al., A purification method for apolipoprotein A-I and A-II, Analytical Biochemistry, 178. p. 301-305 (1989)).

EP0329605 to Rotkreuzstiftung Zentrallaboratorium Blutspendedienst SRK and Lerch et al., Isolation and properties of apolipoprotein A for therapeutic use, Protides Biol. Fluids, 36, p. 409-416 (1989), relate to the preparation of apolipoproteins from fractions of human blood plasma containing lipoproteins. Both publications report that precipitates B and IV of a cold ethanol fractionation process can be used as starting material for producing ApoA-I. Use is made of buffers containing high ethanol concentrations, optionally with an organic solvent, for precipitating contaminants. The precipitates are solubilized in guanidine hydrochloride, which is subsequently removed by gel filtration or diafiltration. An anion-exchange chromatography step is included to bind the contaminants, while the ApoA-I passes through. Optionally it is proposed to concentrate ApoA-I by adsorption onto a second ion exchange resin.

WO9807751 also reports the use of ion-exchange chromatography for the isolation of ApoA-I.

Alpha-1-antitrypsin (AAT), a major serine endopeptidase inhibitor, is present in human plasma at a concentration of about 1.9 to 3.5 g/l. This glycoprotein of about 53 kDa is produced in the liver and inhibits neutrophil elastase, an enzyme involved in the proteolysis of connective tissue especially in the lung. AAT has three N-glycosylation sites at asparagine residues 46, 83, and 247, which are glycosylated by mixtures of complex bi- and triantennary glycans. This results in multiple AAT isoforms, having isoelectric points in the range of 4.0 to 5.0. Protease inhibition by AAT is an essential component of the regulation of tissue proteolysis, and AAT deficiency is implicated in the pathology of several diseases. Individuals who inherit an AAT deficiency, for example, have an increased risk of suffering from severe early-onset emphysema, the result of unregulated destruction of lung tissue by human leukocyte elastase. The administration of exogenous human AAT has been shown to inhibit elastase and is associated with improved survival and a reduction in the rate of decline of lung function in AAT-deficient patients (Crystal et al., Am. J. Respir. Crit. Care Med. 158: 49-59 (1998); see R. Mahadeva and D. Lomas, Thorax 53:501-505 (1998) for a review.)

Because of its therapeutic utility, commercial AAT production has been the subject of considerable research. Much progress has been made in the production of recombinant AAT in *E. coli* (R. Bischoff et al., Biochemistry 30:3464-3472 (1991)), yeast (K. Kwon et al., J. Biotechnology 42:191-195 (1995); Bollen et al., U.S. Pat. No. 4,629,567), plants (J. Huang et al., Biotechnol. Prog. 17:126-33 (2001)), and by secretion in the milk of transgenic mammals (G. Wright et al., Biotechnology, 9:830-834 (1991); A. L. Archibald, Proc. Natl. Acad. Sci. USA, 87:5178-5182 (1990)). However, the isolation of AAT from human plasma is presently the most efficient practical method of obtaining AAT in quantity, and human plasma is the only FDA-approved source.

A number of processes for isolating and purifying AAT from human plasma fractions have been described, involving combinations of precipitation, adsorption, extraction, and chromatographic steps. Most published processes for AAT isolation begin with one or more fractions of human plasma known as the Cohn fraction IV precipitates, e.g. Cohn fraction IV, or more specifically fraction $IV_1$, and fraction $IV_{1-4}$ as well as precipitates of Kistler-Nitschmann supernatant A or A-I, which are obtained from plasma as a paste after a series of ethanol precipitations and pH adjustments (E. J. Cohn et al., J. Amer. Chem. Soc., 68:459-475 (1946); P. Kistler, H. S, Nitschmann, Vox Sang., 7:414-424 (1962)).

Glaser et al., Preparative Biochemistry, 5:333-348 (1975), describes a method for isolating AAT from Cohn fraction $IV_1$ paste. The paste is stirred in a phosphate buffer at pH 8.5 in order to reactivate the AAT, which is largely inactivated by the pH of 5.2 employed in the Cohn fractionation. After dialysis and centrifugation, the supernatant is subjected to two rounds of anion exchange chromatography at pH 6.0 to 7.6 and at pH 8.6, followed by further chromatographic processing at pH 7.6 and at pH 8.0, to produce AAT in about a 30% overall yield.

Lebing and Chen, in U.S. Pat. No. 5,610,285, describe a purification process that employs an initial anion exchange chromatography step, followed by cation exchange chromatography at low pH and low ionic strength, to purify human AAT from plasma and plasma fractions. The cation chromatography takes advantage of the fact that active AAT does not bind to the ion exchange column under these conditions while contaminating proteins, including denatured AAT and albumin, are retained.

Coan, in U.S. Pat. No. 4,697,003, describes a method for isolating AAT from various Cohn plasma fractions comprising the removal of ethanol and salts from an AAT-containing fraction, followed by anion-exchange chromatography on DEAE cellulose or a similar material under conditions so that the AAT is retained on the column while undesired proteins are eluted. Coan also describes "pasteurization" at about 60° C. or more for about 10 hours, which is stated to be sufficient to render hepatitis viruses non-infective.

Glaser et al., in Anal. Biochem., 124:364-371 (1982) and also in European Patent Application EP 0 067 293, describes several variations on a method for isolating AAT from Cohn fraction IV, precipitate that comprises the steps of (a) dissolving the paste in a pH 8.5 buffer, (b) filtering, (c) adding a dithiol such as DTT, and (d) precipitating denatured proteins with ammonium sulfate. Glaser et al. describe one variation in which treatment with DTT is carried out in the presence of 2.5% AEROSIL™ fumed silica, prior to precipitation with 50% saturated ammonium sulfate. Recovery of AAT was as good as it was in the absence of the silica, and the purification factor was improved by about 70%. Glaser states that Aerosil 380 may be used in the process to remove alpha- and beta-lipoproteins.

Mattes et al., in Vox Sanguinis 81:29-36 (2001), and in PCT Publication WO 98/56821, U.S. Pat. No. 6,974,792 and U.S. Patent Publication 2002/0082214, discloses a method for isolating AAT from Cohn fraction IV that involves ethanol precipitation, anion exchange chromatography, and adsorption chromatography on hydroxyapatite. The latter step is reported to remove inactive AAT, providing a product with very high specific activity, which, according to the inventors, is due to the enrichment of AAT isoforms with pl values of 4.3 and 4.4 said not to be present in other high purity AAT preparations known in the art.

Key et al. in PCT Publication WO 04060528 discloses a method for isolating AAT from AAT comprising fractions, preferentially from Cohn fraction $IV_{1-4}$, suspending the AAT-containing protein mixture in a buffer under conditions that permit the AAT to be dissolved; contacting the resulting suspension with a disulfide-reducing agent to produce a reduced suspension; contacting the reduced suspension with an insoluble protein-adsorbing material; and removing insoluble materials from the suspension, further to be combined with ionic exchange chromatography and hydrophobic interaction chromatography.

Ralston and Drohan, in U.S. Pat. No. 6,093,804 describe a method involving the removal of lipoproteins from an initial protein suspension via a "lipid removal agent," followed by removal of "inactive AAT" via elution from an anion-exchange medium with a citrate buffer. The lipid removal agent is stated to be MICRO CEL™ E or Chromosorb E™, a synthetic hydrous calcium silicate. In the presence of a non-citrate buffer, the anion-exchange medium binds active AAT while allowing "inactive AAT" to pass through. A citrate buffer is specified for subsequent elution of the AAT from the anion exchange medium, and also for later elution from a cation-exchange medium. Ralston and Drohan do not describe the use of a disulfide-reducing agent. The process is stated to provide AAT with a product purity of >90% (and >90% of the purified AAT to be active AAT) and manufacturing scale yields of >70%. Ralston and Drohan state that Cohn Fraction $IV_1$ preparations in particular contain a significant amount of ApoA-I and point out that this has the effect of inhibiting column flow and capacity during purification. They report that treatment of the protein mixture suspension with the above mentioned "lipid removal agent" removes ApoA-I.

Bauer describes a method of AAT purification in PCT Publication WO 05027821 starting from different Cohn fractions, preferably fraction IV-1, the removal of contaminating substances (i.e., lipids, lipoproteins and other proteins), and separation of active from inactive AAT by sequential chromatography steps. Bauer does not mention that purifying ApoA-I would be desirable; to the contrary, Bauer points out that ApoA-I inhibits column flow and reduces capacity during purification and proposes to remove the contaminating ApoA-I by binding it to fumed silica (Aerosil™). Bauer neither discloses whether ApoA-I can be eluted from fumed silica nor suggests that this would be desirable.

While AAT is an effective treatment for emphysema due to alpha-1-antitrypsin deficiency, treatment is very costly (currently about $25,000 per year) due to the limited supply of protein and the complex manufacturing process. There remains a need for more efficient and cost-effective methods for isolating human AAT from plasma and other complex protein mixtures containing AAT.

In almost all purification methods for AAT discussed above, lipoproteins, including ApoA-I, are discarded as a contaminant, usually being still bound to a lipid removal agent. On the other hand, published purification methods for ApoA-I discard AAT in a mixture with many other plasma proteins.

Purification of both AAT and ApoA-I from the same fraction of human plasma, is only mentioned in the above cited U.S. Pat. No. 6,093,804, where it is stated that ApoA-I can be separated from AAT by adsorption to a synthetic hydrous calcium silicate and subsequently eluted with 0.5 N NaOH before further downstream processing. It is not disclosed how pharmaceutical purity grade AAT and ApoA-I can be obtained from a purification process starting from the same human plasma fraction. In fact, a later application from the same applicant (American Red Cross, PCT Publication WO 05027821) points out that this method is not suitable for large-scale preparation, specifically pointing out that the method as described in U.S. Pat. No. 6,093,804 is only efficient for small to mid-scale processing of source material in the range of a few kilograms.

Moreover, elution of ApoA-I with 0.5 N NaOH as proposed in U.S. Pat. No. 6,093,804 creates a high alkaline environment of about pH 13.69 that will lead to the partial or even complete deamidation of ApoA-I (see Johnson A. et al., Biochem. Biophys. 1989, 268(1): 276-86) and possibly to irreversible denaturation. As biopharmaceuticals usually loose their biological activity and worse are prone to eliciting immunogenic reactions if deamidated and/or denatured, there is a need to develop further methods of purification that cause less or no denaturation.

SUMMARY OF THE INVENTION

The current invention discloses methods for separating AAT from ApoA-I at the initial stage of purification, so that the same starting material can be used as a source for both proteins and methods to further purify the separated AAT and ApoA-I to pharmaceutical grade purity. In other words the current invention discloses a method for purifying ApoA-I and AAT comprising the steps of i) treating a starting material comprising ApoA-I and AAT to separate an ApoA-I containing fraction from an AAT containing fraction; ii) purifying ApoA-I to pharmaceutical grade purity from the ApoA-I containing fraction; and
iii) purifying AAT to pharmaceutical grade purity from the AAT containing fraction.

By "pharmaceutical grade purity" in the sense of the invention a purity of more than 75%, preferentially more than 85% and even more preferentially more than 95% is meant.

The methods of the invention minimize deamidation and denaturation. This may be achieved by keeping the pH below 13.69, at or below 13, at or below 12, or at or below 11 at each step of the purification of both proteins or, alternatively, minimizing the time the proteins are incubated at a pH of 11 or higher. In one embodiment, the deamidation and denaturation of ApoA-I and AAT can be minimized by ensuring that the pH is from 7 up to and including 12. In another embodiment, the pH range is from 8 up to and including 11. In yet another embodiment the pH range is from 9 up to and including 10. Some specific, but non-limiting examples of pH values that minimize deamidation and denaturation of ApoA-I and AAT, include pH 8.0, 8.5, 9.0, 9.5, 10, 10.5, and 11. At any point in the specification that refers to the pH remaining below the levels taught above, these ranges and specific pH points also apply.

Preventing the deamidation of the proteins leads to less denaturation and reduces the risk that the resulting biopharmaceutical drugs will be immunogenic.

The invention teaches specifically four different methods of achieving this separation and purification of AAT and ApoA-I, all of which are suitable for large-scale purification. Suitable for large-scale purification in the sense of the invention means purification starting from tens of kilograms of a starting material such as a human plasma fraction, for example starting from 50 kilograms or more of a human plasma fraction.

All publications and patent applications specifically referenced herein are incorporated by reference in their entirety. Unless defined otherwise, all technical and scientific terms used herein have the same meaning as commonly understood by one of ordinary skill in the art to which this invention belongs.

The term "AAT" refers to human AAT generally, isolated from human serum. The term is intended to embrace pharmacologically effective naturally occurring variants (see for example, Brantly et al., Am. J. Med. 84 (sup.6A):13-31 (1988)).

The term "ApoA-I" refers to human ApoA-I generally, isolated from human serum. The term is intended to embrace pharmacologically effective naturally occurring variants.

Those of skill in the art will appreciate that methods and materials similar or equivalent to those described herein can be used in the practice of the present invention, and such equivalents are intended to be within the scope of the invention. The embodiments described below are provided by way of example only, and the scope of the invention is not limited to the particular embodiments described.

Any unpurified mixture of proteins containing a substantial amount of AAT and ApoA-I can be used as a starting material for AAT and ApoA-I purification according to the methods of the present invention. According to one embodiment, the AAT- and ApoA-I containing protein mixture can be selected from a fraction of human plasma, particularly from plasma Cohn fractions IV paste. The term "fraction of human plasma" encompasses any starting material containing AAT and ApoA-I obtained by removing one or more plasma components from plasma. In certain embodiments, Cohn Fraction $IV_1$ paste can be the starting material, but the use of similar plasma fractions is contemplated to be within the scope of the present invention. Alternative starting materials include but are not limited to other AAT- and ApoA-1-containing Cohn fractions, precipitates from Kistler-Nitschmann supernatants A or A+I (P. Kistler, H. S. Nitschmann, *Vox Sang.*, 7:414-424 (1962)), and ammonium sulfate precipitates from plasma as described by Schultze et al. in U.S. Pat. No. 3,301,842. A common step to all methods of the invention is that the human plasma fraction is treated in such a way that AAT and ApoA-I are both solubilized.

In one embodiment of the invention, separation and purification of AAT and ApoA-I can be achieved by adjusting the pH and the concentration of a lower aliphatic alcohol in the AAT/ApoA-I suspension so that ApoA-I precipitates whereas AAT remains in solution. The precipitated ApoA-I can be separated from the AAT containing solution. The invention provides novel and advantageous conditions for precipitating ApoA-I from suspensions. Although the art, e.g. Patent Application EP0329605, suggests that the precipitation of ApoA-I with lower aliphatic alcohols might be suitable for large-scale processing, it was found that under the conditions taught in the art, ApoA-I precipitates together with AAT. Also, the yield of AAT decreases and AAT is partially inactivated. The present invention solves the problem of separating ApoA1 from AAT while also preventing loss and inactivation of AAT when separating ApoA-I from solutions comprising both AAT and ApoA-I by precipitating ApoA-I with lower aliphatic alcohols at concentrations between 5% and 25% (v/v) and at a pH between pH 4 to 8.

Certain embodiments of the invention teach methods of separation and purification of AAT and ApoA-I wherein the pH of the AAT/ApoA-I solution, which is treated with an ApoA-I binding agent and may be treated optionally with DTT, is adjusted so that ApoA-I binds to the ApoA-I binding agent. Examples of ApoA-I binding agents include fumed silica (e.g., Aerosil™), lipid removal agent (LRA™) or specific ApoA-I binding ligands like Cibacron Blue™ derivatives (Ciba); Triazine derivatives (Prometic) or VHH antibody fragments (The Bio Affinity Company). In some embodiments, ApoA-I can be bound to fumed silica. ApoA-I bound to fumed silica can be separated from the AAT containing solution and in a next step ApoA-I can be eluted from the fumed silica. In various embodiments, ApoA-I can be eluted from the fumed silica at a pH of less than pH 13.69, at or below 13, at or below 12, or at or below 11.

In some embodiments, the invention teaches a method of separation and purification of AAT and ApoA-I wherein the AAT/ApoA-I solution is treated with dithiothreitol (DTT) and fumed silica (Aerosil 380) at conditions where neither protein binds. The soluble AAT/ApoA-I fraction is separated from the precipitated fumed silica/contaminating proteins yielding an AAT and ApoA-I containing supernatant. AAT and ApoA-I are further purified with ion exchange chromatography and separated during a subsequent hydrophobic interaction chromatography step.

In various embodiments, the invention teaches a method of separation and purification of AAT and ApoA-I wherein the AAT/ApoA-I solution is passed through an anion-exchange column at conditions where neither ApoA-I nor AAT bind to the ion-exchange column, the flow through being subsequently contacted with a hydrophobic interaction chromatography (HIC) column under conditions such that ApoA-I can bind and AAT can remain soluble and can be separated from ApoA-I in the flow-through fraction.

After the separation of AAT and ApoA-I, the respective AAT and ApoA-I containing solutions may be further processed by any of the methods known in the art for protein purification, particularly by methods already known to be suitable for purifying of AAT or ApoA-I.

In certain embodiments, virus reduction steps can be performed during or after the protein purification steps described in detail below, the purified proteins can be sterilized and formulated in pharmaceutical suitable storage buffers and either lyophilized or stored as liquid formulations.

Other objects, features and advantages will become apparent from the following detailed description. The detailed description and specific examples are given for illustration only since various changes and modifications within the spirit and scope of the invention will become apparent to those skilled in the art from this detailed description. Further, the examples demonstrate the principle of the invention and cannot be expected to specifically illustrate the application of this invention to all the examples where it will obviously useful to those skilled in the prior art.

BRIEF DESCRIPTION OF THE FIGURE

FIG. 1: Flow diagram illustrating an embodiment of the separation of ApoA-I and AAT as described in detail in example 2.

DETAILED DESCRIPTION OF THE INVENTION

The current invention provides methods for separating AAT from ApoA-I at the initial stage of purification, so that the same starting material can be used for both proteins. The invention also provides methods to further purify the separated AAT and ApoA-I to pharmaceutical grade purity at large scale respectively. The methods of the invention minimize deamidation and denaturation. This can be achieved by keeping the pH below 13.69, at or below 13, at or below 12, or at or below 11 at each step of the purification of both proteins or alternatively minimizing the time the proteins are incubated at a pH of 11 or higher. The duration of this exposure is to be minimized, e.g., in certain embodiments the time at pH values at or above pH 11 should not exceed more than 5 h. In some embodiments, the time at pH values at or above pH 11 should not exceed 1 h. In other embodiments, the time at pH values at or above pH 11 should not exceed 30 min at 25° C. At higher temperatures acceptable exposure times are even shorter, at lower temperatures acceptable exposure times might be longer. Preventing deamidation of the proteins to be purified leads to considerably less denaturation and greatly reduces the risk that the resulting biopharmaceutical drugs will be immunogenic. In one embodiment, the deamidation and denaturation of ApoA-I and AAT can be minimized by ensuring that the pH is from 7 up to and including 12. In another embodiment, the pH range is from 8 up to and including 11. In yet another embodiment the pH range is from 9 up to and including 10. Some specific, but non-limiting examples of pH values that minimize deamidation and denaturation of ApoA-I and AAT, include pH 8.0, 8.5, 9.0, 9.5, 10, 10.5, and 11.

Any unpurified mixture of proteins containing a substantial amount of AAT and ApoA-I can be used as a starting material for AAT and ApoA-I purification according to the methods of the present invention. According to one embodiment, the AAT and ApoA-I containing protein mixture can be selected from a fraction from human plasma, particularly from plasma Cohn fraction IV paste. In certain embodiments, Cohn Fraction IV, paste is the starting material, but the use of similar plasma fractions is contemplated to be within the scope of the present invention. Alternative starting materials include but are not limited to other AAT- and ApoA-1-containing Cohn fractions, precipitates from Kistler-Nitschmann supernatants A or A-I (Kistler and Nitschmann, Vox Sang., 7:414-424 (1962)), and ammonium sulfate precipitates from plasma as described by Schultze et al. in U.S. Pat. No. 3,301,842.

Cohn fraction $IV_1$ paste can be prepared by cooling human plasma to a temperature between −2° C. to 2° C. and adjusting it to about a pH of 6.9 to 7.5. After adding cold ethanol to a concentration of about 6 to 10% (v/v) and lowering the temperature to about −4° C. to 0° C., a precipitate called Fraction I is formed and then removed by centrifugation or filtration. The filtrate or supernatant from the above procedure can then be adjusted to about a pH of about 6.7 to 7.1 and cold ethanol can be added to a concentration of about 18 to 22% (v/v). The temperature can then be lowered to about −7° to −3° C., and the mixture again subjected to centrifugation or filtration. The precipitate that forms now, called Fraction II+III, can be removed and used to purify other proteins. This second filtrate or supernatant can then be adjusted to a pH of about 5.0 to 5.1, the ethanol concentration adjusted to about 20.0 to 22.0% (v/v), and the temperature adjusted to about −6° C. to −3° C. Fraction $IV_1$ now precipitates and can be removed by centrifugation or filtration, and stored until needed in the form of a paste. Fraction $IV_1$ paste contains AAT, ApoA-I, as well as other contaminating proteins and lipids.

The methods of the invention for purifying ApoA-I and AAT are suitable for large-scale purification. Suitable for large-scale purification in the sense of the invention means purification of ApoA-I and AAT in high yield and purity even when starting from tens of kilograms of starting material for example from tens of kilograms of a human plasma fraction. In some embodiments, purification starts from more than 50 kg of a human plasma fraction. In some embodiments, purification starts from more than 50 kg of Cohn Fraction $IV_1$, the latter being equivalent to a starting volume of human plasma of about 900 liters. Also starting volumes of human plasma in the range between 3000 and 4000 Liters or more can be used for the methods of the invention. AAT purified according to the present invention has a purity of >96% as determined with SDS-Page and immunological assays such as ELISA or nephelometry. Typically, about 79 to 99% of the purified AAT is active, on average about 90%. The recovery based on the functionally active AAT content of Cohn Fraction $IV_1$ is about 40 to 60% or approximately 20 to 40% of the normal content in human plasma.

ApoA-I purified according to the present invention has a purity of at least 75%. Using certain embodiments, the purity of ApoA-I is higher than 85%. The yield is at least 15%. Using certain embodiments, the yield is at least 30% as compared to the ApoA-I content in plasma.

In some embodiments of the invention, separation and purification of AAT and ApoA-I can be achieved by adjusting the pH and the concentration of a lower aliphatic alcohol, e.g., ethanol, in an AAT/ApoA-I solution so that ApoA-I precipitates whereas AAT remains in solution. The precipitated ApoA-I can be separated from the AAT containing solution. EP0329605 reports that ApoA-I can be precipitated from resuspended human plasma fractions by precipitation with lower aliphatic alcohols.

We have now found that the concentrations below 40% (v/v) of a lower aliphatic alcohol under the conditions as disclosed in EP0329605 to precipitate ApoA-I do not lead to a separation of ApoA-I and AAT and also lead to a concomitant loss and inactivation of AAT and are therefore not suitable for a purification method for both proteins. Lower aliphatic alcohols in the sense of the invention means aliphatic alcohols with C1- to C4, for example, methanol, ethanol, propanol and butanol.

It has now been surprisingly found that at a pH of 4.5 to 6.5 ApoA-I can be precipitated at concentrations of a lower aliphatic alcohol, e.g., ethanol, as low as approximately 5 to 25% (v/v) while AAT remains in solution and retains its activity. In some embodiments, the pH is 5 to 6. In certain embodiments, the concentration of lower aliphatic alcohol is about 7 to 15% (v/v). In certain embodiments, the concentration of lower aliphatic alcohol is about 8 to 14% (v/v). At higher pH, e.g., above 6.5, precipitation of ApoA-I will be reduced, whereas at a lower pH, e.g. below 4.5 AAT will increasingly be precipitated as well. At a lower concentration of a lower aliphatic alcohol, e.g., lower than 5% (v/v) ethanol concentration ApoA-I will not precipitate, whereas at higher concentration of a lower aliphatic alcohol, e.g., at ethanol concentrations higher than 25% (v/v) AAT will increasingly be precipitating as well. In various embodiments, the temperature during the precipitation step(s) can be kept below about 10° C.

In addition to allowing the separation of ApoA-I and AAT and preventing loss and inactivation of AAT while precipitating ApoA-I, the method of the invention provides a more economical way of precipitating ApoA-I with lower aliphatic alcohols than suggested in the related art. Also, the reduced explosion hazard due to the use of lower concentrations of the lower aliphatic alcohol leads to lower costs in the construction of the manufacturing unit for the precipitation step.

After the precipitation step AAT and ApoA-I can be separately purified in one or more processing steps to pharmaceutical grade purity. After the separation of AAT and ApoA-I, the AAT- and ApoA-I containing solutions can be further processed by any of the methods known in the art for protein purification, for example, methods already known to be suitable for purification of AAT or ApoA-I respectively.

In some embodiments of the invention, Cohn Fraction $IV_1$ can be resuspended in about 50-150 mM Tris, 0-30 mM NaCl, at a pH between about 8.0 to 10.0 and stirred for at least 1 hour at about 0 to 10° C. In various embodiments, the pH can be between about 8.8 and 9.6. In certain embodiments, the solution of resuspended Cohn Fraction IV, can be stirred for about 2-3 hours. About 6 to 18 kg, or 12 to 16 kg of buffer can be used per kg of Cohn fraction $IV_1$. As an optional step to maximize AAT yield the Tris buffer suspension can be heated to a temperature of about 40 to 45° C. for a period of about 1 to 1.5 hours, then cooled to about 0 to 10° C. again.

The Tris buffer suspension can then be cooled to a temperature of about 0° C. to 2° C. ApoA-I can then be precipitated by adjusting the suspension of ApoA-I and AAT to a pH of about 5.0 to 6.0 and an ethanol concentration of 8% to 14% (v/v). This adjustment can be achieved, for example, by adding a predetermined amount of ethanol and sodium acetate/acetic acid solution to the Tris buffer suspension. The ethanol/acid solution can be added over a period of about 30 to 60 minutes as the temperature is cooled to about 0° C. to −7° C. and then these conditions are maintained for a period of about 2 to 4 hours. In order to facilitate subsequent separation of ApoA1 via filtration, a filter aid, such as C1000 can be added and the mixture can then be stirred for a minimum of 15 minutes. The soluble AAT containing filtrate can be separated from the insoluble ApoA-I material by filtration, preferentially utilizing a filter press. Alternatively, the insoluble ApoA-I material can be separated by centrifugation.

AAT in the filtrate or supernatant of the above described separation method can then be further purified. In some embodiments, the AAT filtrate can be adjusted to about 0° C.-8° C. and a pH of about 8.8 to 9.6. After pH adjustment, DTT can be added to a concentration of about 15-30 mM. The DTT treated filtrate can then be mixed for about 2 to 4 hours at about 0 to 10° C., while maintaining the pH at about 8.8 to 9.6. Then fumed silica can be added to the solution at a concentration of approximately 16.7 g/L plasma equivalent in the plasma containing paste fraction. The suspension can then be stirred for at least 30 minutes at about 0 to 10° C., within the pH range of about 8.8 to 9.6. In some embodiments, the solution is stirred for about 1-4 hours. At this stage remaining impurities of the AAT filtrate can bind to the suspension of fumed silica, which then forms a precipitate. As fumed silica, for example, Aerosil™ can be used. AAT, which remains in solution, can be separated from the precipitated fumed silica and contaminating proteins using a filter press, optionally after adding a filter aid like C1000, yielding purified AAT filtrate. If a filter aid is used, the amount can be about 3 kg of filter aid per 1 kg of fumed silica. In various embodiments, the suspension can be recirculated through the filter press until the desired level of clarity is obtained.

In embodiments described below, the filtrate can first be subjected to ion exchange chromatography ("IEC") with salt gradient elution. The chromatography column can contain an anion exchange resin that consists of a porous resin support matrix to which positively charged groups are covalently attached. These positively charged groups reversibly bind anions, including proteins with anionic groups such as AAT.

AAT, and other proteins that have a net negative charge at the pH of the eluting buffer, can bind to the IEC column. Contaminating proteins having little or no negative charge can pass through the anion exchange resin column without binding and exit with the column effluent. Those contaminating proteins that do bind to the column are then separated from the AAT by gradient elution. The salt concentration can be gradually increased as the column is eluted in order to release sequentially the various proteins that are bound to the resin.

The AAT final filtrate can be applied directly onto a chromatography column containing an anion exchange resin equilibrated with an IEC equilibration buffer (approximately 50 mM Tris and a pH of about 8.6-8.9). The column can be loaded to approximately 50-70% of a pre-determined protein capacity with the AAT final filtrate. Contaminants can then be removed from the column by washing the column with an IEC wash buffer (for example, approximately 50 mM Tris, about 25-65 mM NaCl, and pH about 7.1-7.7), and AAT can be subsequently eluted using an IEC elution buffer (for example, approximately 50 mM Tris, about 70-120 mM NaCl, and pH about 7.1-7.7).

In certain embodiments, described below, the AAT-containing eluate from the IEC column can be subjected to hydrophobic interaction chromatography ("HIC"). This type of chromatography employs a support matrix to which moieties are covalently attached. In an aqueous environment, these hydrophobic moieties can bind reversibly to hydrophobic molecules, such as the contaminating proteins remaining in the IEC eluate. AAT is relatively non-hydrophobic. Therefore, the majority of the AAT can flow through the column during the elution of the column with buffer, while the more hydrophobic contaminating proteins remain bound to the column. The column effluent thus contains the purified AAT. In practice, AAT has been found to have a slight affinity for certain HIC column media, and in such cases further elution with several volumes of wash buffer may be desirable in order to recover substantially all of the AAT in the originally applied sample.

The eluate from the IEC column can be prepared for HIC by adding ammonium sulfate to a final concentration of approximately 0.9 to 1.1 M. The solution can then be filtered and applied to a hydrophobic interaction column, which has been equilibrated with a HIC Wash Buffer (e.g., approximately 50 mM Tris, about 1M ammonium sulfate, pH about 7.3-7.5). The column can then be loaded within a range of about 25-75 grams protein/L gravity settled resin. During the load, AAT does not bind to the hydrophobic column matrix and flows through the column. At the completion of the load, unbound AAT remaining in the packed column can be washed off the column using the HIC Wash Buffer. The combined column flow through and subsequent wash can be concentrated by ultra-filtration, and diafiltered into a phosphate buffer (about 40 mM sodium phosphate and approximately a pH between 7.2-7.6). The final AAT concentration is preferably no greater than 7% protein.

After such additional purification steps as are required to reach the desired level of purity and activity, the AAT solution can then be concentrated and sterilized. In various embodiments, the AAT can be at a pharmaceutically acceptable level of purity and activity after the hydrophobic interaction chromatography, and no additional steps may be necessary. In some embodiments, concentration can be accomplished by ultrafiltration followed by dialysis filtration (diafiltration). In these techniques, solvent and dissolved salts and small molecules are passed through a filtering membrane, leaving behind a more concentrated protein solution. Remaining salts and small molecules in the protein solution can then be exchanged with a different buffer by continuous addition of several volumes of the new buffer to the product, while maintaining a constant product volume by continuously passing solution through the same membrane.

The AAT can then be provided with a pharmaceutically acceptable buffer, and stored either in liquid form or lyophilized by methods known in the art, for example, by methods known to be suitable for preparing AAT therapeutic formulations.

Proteins isolated from mammalian sources may contain pathogenic viral contaminants, and it can be desirable to reduce or eliminate such contamination in pharmaceutical compositions. Methods of viral reduction are known to those of skill in the relevant arts. The methods contemplated to be applicable to the present invention include, but are not limited to, pasteurization, irradiation, solvent/detergent treatment, disinfection, filtration, and treatment with supercritical fluids. Solvent/detergent treatment can be carried out, for example, by contacting a protein solution with a polyoxyethylene sorbitan ester and tributyl phosphate (see U.S. Pat. No. 4,820,805; see also WO 95/35306 for application of the method to an AAT composition.) Disinfection of a protein solution can be carried out by exposing the solution to a soluble pathogen inactivating agent, for example as disclosed in U.S. Pat. Nos. 6,106,773, 6,369,048, and 6,436,344, or by contact with an insoluble pathogen inactivating matrix, for example as disclosed in U.S. Pat. No. 6,096,216 and references therein. Filtration can be through 15-70 nm ultrafilters (e.g., VirAGard™ filters, A/G Technology Corp.; Planova™ filters, Asahi Kasei Corp.; Viresolve™ filters, Millipore Corp.; DV and Omega™ filters, Pall Corp, as well as hollow fibre filters from GE Healthcare) Irradiation can be with ultraviolet or gamma radiation; see for example U.S. Pat. No. 6,187,572 and references therein. Inactivation of viruses by treatment with supercritical fluids is described in U.S. Pat. No. 6,465,168. Pasteurization of a protein solution can be accomplished by heating within the limits dictated by the thermal stability of the protein to be treated. In the case of AAT, pasteurization can usually be accomplished by heating to about 60-70° C. In some embodiments, described below, viral reduction of the AAT concentrate can be carried out by pasteurization and ultrafiltration. Stabilizing additives can be added to protect the AAT from thermal degradation during the pasteurization step, as disclosed for example in U.S. Pat. No. 4,876,241. Sucrose and potassium acetate can be added as stabilizers, and the stabilized AAT solution can then be pasteurized at about 60° C. to reduce viral contamination. The amount of sucrose can be at least 40%, at least 50%, or about 60% by weight. Use of less than 40% sucrose has been found to result in undesirable levels of aggregation of AAT. The amount of potassium acetate can be at least 4%, at least 5%, or about 6% by weight.

After viral reduction, the AAT solution can optionally be diluted and ultrafiltered, then re-concentrated and sterilized, e.g., by filtration. The sterilized AAT-containing concentrate can then be lyophilized to form a therapeutic product. In some embodiments, a lyophilized AAT powder can be prepared in 20 mM sodium phosphate, 45 mM NaCl, 3% mannitol. This composition is suitable as such for injection, but can be lyophilized and stored in glass vials for later reconstitution with sterile water.

The AAT final filtrate is applied directly onto a chromatography column containing an anion exchange resin equilibrated with an IEC equilibration buffer (approximately 50 mM Tris and a pH of about 8.6-8.9). The column is loaded to approximately 50-70% of a pre-determined protein capacity with the AAT final filtrate. Contaminants are then removed from the column by washing the column with an IEC wash buffer (approximately 50 mM Tris, about 25-65 mM NaCl, and pH about 7.1-7.7), and AAT is subsequently eluted using an IEC elution buffer (approximately 50 mM Tris, about 70-120 mM NaCl, and pH about 7.1-7.7).

The final formulation will depend on the viral inactivation step(s) selected and the intended mode of administration. Depending on whether the AAT is to be administered by injection, as an aerosol, or topically, the AAT can be stored as a lyophilized powder, a liquid, or a suspension. The composition of a dry powder formulation for inhalation can be, for example, a nominal content per dose of 7.44 mg AAT, 0.059 mg sodium citrate, and 0.001 mg citric acid. Such a formulation is suitable for inhalation administration as described in U.S. Pat. No. 5,780,014, either with a metered dose inhaler or with a pulmonary delivery device such as is disclosed in U.S. Pat. No. 6,138,668.

AAT purified according to the present invention has a purity of >96% as determined by SDS-Page and immunological assays such as ELISA or nephelometry. Typically, about 79 to 99% of the purified AAT is active, on average about 90%. The recovery based on the functionally active AAT content of Cohn Fraction $IV_1$ is about 40 to 60% or 20 to 40% compared to the original content in human plasma.

The AAT purified by this method or any method described below is not enriched in the isomer with a pI of 4.3 to 4.4 as described, for example, in U.S. Pat. No. 6,974,792.

Purified AAT as described in this invention can be formulated into pharmaceutical preparations for therapeutic use. The purified protein may be dissolved in conventional physiologically compatible aqueous buffer solutions to which there may be added, optionally, pharmaceutical excipients to provide pharmaceutical preparations.

Such pharmaceutical carriers and excipients as well as suitable pharmaceutical formulations are well known in the art (see, for example, "Pharmaceutical Formulation Development of Peptides and Proteins", Frokjaer et al., Taylor & Francis (2000) or "Handbook of Pharmaceutical Excipients", 3rd edition, Kibbe et al., Pharmaceutical Press (2000)). In particular, the pharmaceutical composition comprising the polypeptide variant of the invention can be formulated in lyophilized or stable liquid form. AAT can be lyophilized by a variety of procedures known in the art. Lyophilized formulations are reconstituted prior to use by the addition of one or more pharmaceutically acceptable diluents such as, for example, sterile water for injection or sterile physiological saline solution.

Formulations of the composition can be delivered to an individual by any pharmaceutically suitable means of administration. Various delivery systems are known and can be used to administer the composition by any convenient route. The compositions of the invention can be administered systemically. For systemic use, proteins of the invention can be formulated for parenteral (e.g., intravenous, subcutaneous, intramuscular, intraperitoneal, intracerebral, intrapulmonary, intranasal, or transdermal) or enteral (e.g., oral, vaginal, or rectal) delivery according to conventional methods. In certain embodiments, the routes of administration are intravenous, subcutaneous, or intrapulmonary. The formulations can be administered continuously by infusion or by bolus injection. Some formulations encompass slow release systems.

AAT according to the present invention can be administered to patients in a therapeutically effective dose, meaning a dose that is sufficient to produce the desired effect(s), preventing or lessening the severity or spread of the condition or indication being treated without reaching a dose that produces intolerable adverse side effects. The exact dose depends on many factors such as, e.g., the indication, formulation, mode of administration, and has to be determined in preclinical and clinical trials for each indication.

The invention also provides a method of treating an individual suffering from a familiar deficiency of AAT, as well as other indications in which the therapeutic use of AAT may be beneficial, for example, emphysema and cystic fibrosis. The methods comprise administering to said individual a therapeutically effective amount of AAT. A pharmaceutical composition of the invention can be administered alone or in conjunction with other therapeutic agents. These agents can be incorporated as part of the same pharmaceutical.

In specific embodiments of the invention the precipitated ApoA-I as obtained by the methods described above can be further purified as described below.

ApoA-I can be extracted from the precipitate obtained by incubating a suspension of a human plasma protein fraction at about 0 to −2° C. at a pH of about 5 to 6 at concentrations of a lower aliphatic alcohol, e.g., ethanol, of about 8 to 14 in a buffer comprising about 20 mM Tris at pH of 6 to 10 for about 2 h to maximally 24 h at a temperature of 0° C. to 50° C. In some embodiments, the pH of the buffer can be about 8.0. Optionally, water soluble salts can be added at a concentration of about 0-1 M.

To improve the solubilization of ApoA-I, non-ionic detergents (e.g., polysorbate, Brij, octyl-glycosides), ionic detergents (e.g. bile acids), or zwitterionic detergents (e.g. CHAPS™, Zwittergent™) can be added. Depending on the following steps, detergents can be removed or partially removed by, e.g. diafiltration or absorption to appropriate resins (BioBeads™).

The buffered suspension can be stirred, incubated for about 1 to 4 h, and then filtered or centrifuged. ApoA-I as contained in the filtrate or supernatant can be further purified by methods described below.

The pH of the filtrate or supernatant can be adjusted appropriately and ethanol added until the majority of high molecular weight contaminants are precipitated while ApoA-I remains in solution. In certain embodiments, ApoA-I can be precipitated at approx 45% (35-55%) (v/v) ethanol, pH 3.5 (pH 3-5), 10-200 mM NaCl. ApoA-I can also be precipitated by increasing the pH to 5 (pH 4-6) and the ethanol concentration to >50% (50-60%) (v/v).

In a further method according to the present invention, ApoA-I can be isolated from the filtrate or supernatant by precipitation with for example ammonium sulphate: Ammonium sulphate can be added to the ApoA-I extract as a solid or as a concentrated stock solution at a final concentration of about 0.6-1.4 M at a pH range of 6 to 9. The suspension can be incubated for about 2 to 24 h at about 0° C. to 30° C., and the precipitated ApoA-I fraction can be collected by filtration or centrifugation.

Further purification of ApoA-I can then be achieved by methods known in the art, including, for example, binding and eluting ApoA-I from cation- or anion-exchange resins, hydrophobic interaction matrices, and mixed mode resins (e.g., resins having properties that permit them to interact with ionic and hydrophobic sites) under appropriate conditions as can be determined by those skilled in the art. In some embodiments of the invention, conditions can be selected so that in cation-, anion exchange resins, hydrophobic interaction matrices, and/or mixed mode resins; conditions ApoA-I is in the flow through fraction, and the majority of contaminants remains bound to the resin.

Optionally, ApoA-I can be further purified by binding to fumed silica (Aerosil™) and/or Lipid removal agent (LRA™; World Minerals) or by specific ligand adsoption to, e.g., Cibacron™ blue derivatives (Ciba), Triazine derivatives (Prometic), or VHH antibody fragments (The Bio Affinity Company). Elution of ApoA-I from these binding agents can be performed with, for example, detergents, ethanol, chaotropic reagent, high pH, in certain embodiments below pH 13.69, or at or below 13, at or below 12, or at or below 11, or combinations thereof.

ApoA-I purified according to the present invention has a purity of at least 75%, typically higher than 85%. In some embodiments, the yield is at least 15% as compared to the ApoA-I content in plasma. In certain embodiments, the yield is at least 30% as compared to the ApoA-I content in plasma.

In various embodiments, ApoA-I can be subjected to at least one viral reduction step as described above for AAT.

Purified ApoA-I as described in this invention can be formulated into pharmaceutical preparations for therapeutic use. The purified protein can be dissolved in conventional physiologically compatible aqueous buffer solutions to which there can be added, optionally, pharmaceutical excipients to provide pharmaceutical preparations. Such pharmaceutical carriers and excipients as well as suitable pharmaceutical formulations are well known in the art (see for example "Pharmaceutical Formulation Development of Peptides and Proteins", Frokjaer et al., Taylor & Francis (2000) or "Handbook of Pharmaceutical Excipients", 3$^{rd}$ edition, Kibbe et al., Pharmaceutical Press (2000)). In particular, the pharmaceutical composition comprising the polypeptide variant of the invention can be formulated in lyophilized or stable liquid form. ApoA-I can be lyophilized by a variety of procedures known in the art. Lyophilized formulations can be reconstituted prior to use by the addition of one or more pharmaceutically acceptable diluents such as, for example, sterile water for injection or sterile physiological saline solution. In some embodiments, purified ApoA-I can be used therapeutically in the form of reconstituted HDL like particles (rHDL) as described in Lerch et al., Vox Sanguinis 1996; 71: 155-164.

Formulations comprising ApoA-I can be delivered to an individual by any pharmaceutically suitable means of administration. Various delivery systems are known and can be used to administer the composition by any convenient route. In certain embodiments, the compositions of the invention can be administered systemically. For systemic use, the proteins of the invention can be formulated for parenteral (e.g., intravenous, subcutaneous, intramuscular, intraperitoneal, intracerebral, intrapulmonary, intranasal, transdermal) or enteral (e.g., oral, vaginal, rectal) delivery according to conventional methods. In some embodiments, ApoA-I or reconstituted ApoA-I can be administered intravenously. The formulations can be administered continuously by infusion or by bolus injection. Some formulations encompass slow release systems.

ApoA-I according to the present invention can be administered to patients in a therapeutically effective dose, meaning a dose that is sufficient to produce the desired effects, preventing or lessening the severity or spread of the condition or indication being treated without reaching a dose that produces intolerable adverse side effects. The exact dose depends on many factors, such as, e.g. the indication, formulation, and mode of administration and has to be determined in preclinical and clinical trials for each respective indication.

The invention also provides a method of treating an individual suffering from familiar deficiency of ApoA-I, as well as other indications in which the therapeutic use of ApoA-I can be useful, for example, atherosclerosis, cardiovascular disease, cerebral vascular diseases (e.g. stroke), ischemia reperfusion injuries, peripheral vascular diseases, vascular disease associated with diabetes as well as chronic and acute inflammatory diseases and inhibition of excessive coagulation. The method comprises administering to said individual a therapeutically efficient amount of ApoA-I or rHDL.

The pharmaceutical compositions of the invention can be administered alone or in conjunction with other therapeutic agents. These agents can be incorporated as part of the same pharmaceutical.

In certain embodiments, the invention provides a method of separation and purification of AAT and ApoA-I wherein the pH of an AAT/ApoA-I solution is adjusted such that ApoA-I can bind to added ApoA-I binding agents such as, for example, fumed silica (e.g. Aerosil™), Lipid removal agent (LRA™) or specific ApoA-I binding ligands like Cibacron Blue™ derivatives (Ciba); Triazine derivatives (Prometic) or VHH antibody fragments (The Bio Affinity Company). In some embodiments, the fumed silica is the ApoA-I binding agent. ApoA-I bound to fumed silica can be separated from the AAT-containing solution and then ApoA-I can be eluted at a pH of less than pH 13.69, or at or below 13, at or below 12, or at or below 11 from the fumed silica. In one embodiment, ApoA-I can be eluted at a pH of 7 up to and including 12. In another embodiment, the pH can be 8 up to and including 11. In yet another embodiment the pH range can be 9 up to and including 10. Some specific, but non-limiting examples of pH values that ApoA-I can be eluted include pH 8.0, 8.5, 9.0, 9.5, 10, 10.5, and 11. After the separation of AAT and ApoA-I, the AAT and ApoA-1-containing solutions can be further processed by any of the methods known in the art for protein purification, for example, the methods known to be suitable for purification of AAT or ApoA-I.

In certain embodiments of the invention, Cohn Fraction IV$_1$ paste can be suspended in a suspension buffer, e.g., about 50 to 150 mM Tris, 0 to 30 mM NaCl at a pH between about 8.0 to about 10.0, and stirred for a minimum of 1 hour at about 0 to 10° C. In some embodiments, the pH can be between about 9.0 and 9.6. In various embodiments, the suspension can be stirred for 2-3 hours. The amount of buffer can range from 6 kg to 18 kg (or 12 kg to 16 kg) per kg of the plasma-containing fraction (Fraction IV$_1$). As an optional step to maximize AAT yield, the Tris buffer suspension can be heated to a temperature of about 40 to 45° C. for a period of about 1 to 1.5 hours, then cooled to about 0 to 10° C.

The Tris buffer suspension can then be treated with dithiothreitol (DTT) and fumed silica. DTT can be added to the Tris buffer suspension at a concentration in the range of about 15 to 50 mM. The solution can then be stirred for a minimum of about 30 minutes at about 0 to 10° C. at a pH of about 9.0 to 9.6. In certain embodiments, the solution is stirred for about 2-4 hours. The DTT-treated extract can then be adjusted to a pH of about 7.5 to 7.8 using, for example, a dilute hydrochloric acid solution. The fumed silica (for example Aerosil™ 380) can then be added at approximately 16.7 grams/Liter plasma equivalent in the plasma containing fraction. The suspension can then be stirred for at least 30 minutes at low temperature at a pH of about 7.5 to 8.0. In some embodiments, the suspension can be stirred for about 1 to 4 hours. A filter aid such as C1000 can be added at a ratio of about 3 parts filter aid to one part silica, by weight, and the mixture can be stirred for a minimum of about 15 minutes. The soluble AAT fraction can then be separated from the precipitated fumed silica/ApoA-I and contaminating proteins using a filter press, yielding the AAT final filtrate. The AAT filtrate can be processed further while the fumed silica ApoA-I precipitate can be collected for further purification. Alternatively, ApoA-I bound to fumed silica can be separated by centrifugation. Elution of ApoA-I from fumed silica is achieved by incubation in 50-100 mM Tris at a pH of 9 to 10, preferable at a pH of about 9.5. After separating AAT and ApoA-I, both proteins can be purified further for example with methods described above.

In some embodiments, the invention provides a method of separation and purification of AAT and ApoA-I wherein an AAT/ApoA-I solution is treated with dithiothreitol (DTT) and fumed silica (Aerosil™) under conditions where neither protein binds. The soluble AAT/ApoA-I fraction can be separated from the precipitated fumed silica/contaminating proteins yielding an AAT and ApoA-1-containing supernatant. AAT and ApoA-I can be further purified by ion exchange chromatography and separated during a hydrophobic interaction chromatography step.

In various embodiments of the invention, a Fraction $IV_1$ paste can be suspended in a suspension buffer (e.g., 50 to 150 mM Tris, 0-30 mM NaCl, pH between 8.0 to about 10.0) and stirred for a minimum of 1 hour at 0-10° C. In some embodiments, the pH of the suspension buffer can be between 9.0 and 9.6. In certain embodiments, the suspension can be stirred for 2-3 hours. The amount of buffer used can range from 6 to 18 kg's (or 12-16 kg's) per kg of the plasma-containing fraction (Fraction $IV_1$). The Tris buffer suspension can then be heated to a temperature of 40 to 45° C. for a period of 1 to 1.5 hours, then cooled to 0 to 10° C.

The Tris buffer suspension can then be treated with dithiothreitol (DTT) and fumed silica (Aerosil™). DTT can be added to the Tris buffer suspension at a concentration in the range of about 15 to 50 mM. The solution can then be stirred for at least about 30 minutes at a temperature of about 0-10° C. at a pH of about 9.0 to 9.6. In some embodiments, the solution can be stirred for about 2-4 hours. The fumed silica (e.g., Aerosil™) can then be added at approximately 16.7 grams/Liter plasma equivalent in the plasma containing paste fraction. The suspension can then be stirred for at least about 30 minutes at about 0 to 10° C., while maintaining a pH of about 9.0 to 9.6. In some embodiments, the solution can be stirred for about 1-4 hours. A filter aid such as C1000 can be added at a ratio of about 3 parts filter aid to one part fumed silica, by weight, and the mixture can be stirred for a minimum of about 15 minutes. The soluble AAT/ApoA-I fraction can be separated from the precipitated fumed silica/contaminating proteins, for example, using a filter press, yielding a AAT/ApoA-I filtrate. Alternatively other modes of separating the fumed silica, for example, centrifugation, can be employed.

AAT and ApoA-I can be further purified using ion exchange chromatography and hydrophobic interaction chromatography as described above, except that, during the hydrophobic interaction chromatography (HIC) step, ApoA-I is finally eluted with water after AAT has been washed out with a wash buffer comprising 50 mM Tris, 7.5 M ammonium sulfate at a pH of about 7.3 to 7.5. The AAT combined column flow through and subsequent wash are concentrated by ultrafiltration, and diafiltered into a phosphate buffer (about 40 mM sodium phosphate and a pH of about 7.2-7.6). The final AAT concentration is preferably no greater than 7% protein. AAT elutes in pharmaceutical grade purity from the HIC column.

ApoA-I as eluted from fumed silica can then be further purified as described above.

In some embodiments, the invention provides a method of separation and purification of AAT and ApoA-I wherein an AAT/ApoA-I solution is treated with DTT and fumed silica and then passed through an anion-exchange column under conditions where neither ApoA-I nor AAT bind to the ion-exchange column, the flow through being contacted with a HIC column under conditions so that ApoA-I binds and AAT remains soluble and is separated from ApoA-I in the flow-through fraction. After the separation of AAT and ApoA-I, the AAT- and ApoA-I containing solutions can be further processed by any of the methods known in the art for protein purification, for example, by methods known to be suitable for purification of AAT or ApoA-I.

In certain embodiments, Cohn Fraction $IV_1$, paste can be suspended with buffer as described above, treated with DTT and Aerosil™, and filtered. The pH of the AAT/ApoA-I filtrate can be adjusted to about 7.1 to 7.7, for example, by the addition of a dilute hydrochloric acid solution. The conductivity of the AAT/ApoA-I filtrate can then be adjusted to approximately 15 mS/cm at 22.0° C. by, for example, the addition of a 2 M NaCl solution. The pH/conductivity adjusted AAT/ApoA-I filtrate can then be applied directly onto a chromatography column containing an anion exchange resin equilibrated with an equilibration buffer (e.g., about 50 mM Tris, approximately pH 7.4, about 15 mS/cm conductivity). Contaminating proteins can be bound to the column while AAT and ApoA-I flow through.

The AAT/ApoA-I flow through can then be prepared for HIC by adding ammonium sulfate to a final concentration of about 0.9M to 1.1 M. The solution can be filtered and applied to an HIC column that has been equilibrated with an HIC wash buffer. Initial elution during the load can provide an AAT-containing effluent, and elution with additional wash buffer can remove any AAT retained in the column. The combined effluent and washes can be concentrated, for example, by ultrafiltration, and diafiltered into a phosphate buffer. In some embodiments, the final AAT concentration is no higher than 7% protein. Once the AAT fraction is removed, additional impurities can be washed off of the column with a 0.1 to 0.2M ammonium sulfate solution, and then the ApoA-I can be eluted from the column utilizing water. AAT elutes in pharmaceutical grade purity from the HIC column. ApoA-I and AAT can be further purified, for example, using the methods described above.

EXAMPLES

Example 1

Preparation of the Cohn Fraction $IV_1$ Precipitate

Human plasma was cooled to about 0° C. and adjusted to pH of about 7.2. Cold ethanol was added to a concentration of about 8% (v/v), and the temperature was lowered to approximately −2° C. The precipitate that formed (Fraction I) was removed by centrifugation or filtration.

The filtrate or supernatant from the above procedure was adjusted to about pH 6.9, and cold ethanol was added to a concentration of approximately 20% (v/v). The temperature was then lowered to 5° C., and the mixture was again subjected to either centrifugation or filtration. The precipitate that formed (Fraction II+III) was set aside for other purposes.

The filtrate or supernatant from the above procedure was adjusted to a pH of approximately 5.05, and the ethanol concentration was adjusted to 21% (v/v). The temperature was adjusted to −5° C. The precipitate that formed (Fraction $IV_1$) was removed by centrifugation or filtration and stored until needed in the form of a paste. This Fraction $IV_1$ paste contains AAT, ApoA-I, as well as contaminating proteins and lipids.

Example 2

Purification of ApoA-I and AAT Involving Precipitation of ApoA-I 2.1 Separation of ApoA-I and AAT:

2.1.1 Fraction $IV_1$ Extraction and Precipitation of the ApoA-I Fraction

The fraction $IV_1$ material was suspended in a suspension buffer (100 mM Tris, pH 9.6) and stirred for 2 hours at 2-8° C. The amount of buffer used was 15 kg's of buffer per kg of the plasma-containing fraction. The suspension was then cooled to approximately 0° C. and an amount of an ethanol and sodium acetate/acetic acid solution was added to the Tris buffer suspension to yield a suspension having a pH of 5.4 and an ethanol concentration of 12% (v/v). The ethanol/acid solution was added over a period of 30 minutes as the temperature was cooled to approximately −4° C. The pH/ethanol conditions were then maintained for 2 hours. The filter aid C1000 was added at 100 grams filter aid/Kg of Fraction $IV_1$ precipitate. The mixture was then stirred for about 15 minutes. The soluble AAT material (AAT Filtrate) was separated from the insoluble ApoA-I material by filtration with a filter press (ApoA-I Precipitate).

2.2 Further Purification of AAT 2.2.1 Purification with DTT and Silica

As the temperature of the AAT Filtrate was adjusted to approximately 5° C., the pH of the filtrate was adjusted to around 9.4 using 1 M NaOH. After pH adjustment, DTT was added to a concentration of 30 mM. The DTT-treated filtrate was then mixed for 2 hours at approximately 5° C. while maintaining a pH of around 9.4. Fumed silica (Aerosil™ 380) was then added to the solution at a concentration of approximately 16.7 g/L plasma equivalent in the plasma-containing paste fraction. The suspension was then stirred for approximately 1 hour at a temperature of around 5° C. and a pH of approximately 9.4. The filter aid C1000 was added at a ratio of 3 kg's/kg of fumed silica, and the mixture was stirred for approximately 15 minutes. The soluble AAT product was separated from the precipitated fumed silica and contaminating proteins using a filter press, yielding the AAT final filtrate. The suspension was recirculated through the filter press until the desired level of clarity was obtained.

2.2.2 Ion Exchange Chromatography

The AAT final filtrate was applied directly onto a chromatography column containing TMAE Fractogel equilibrated with an IEC equilibration buffer (50 mM Tris, pH 8.8). The column was loaded to approximately 65% of its protein capacity with the AAT final filtrate. Contaminants were removed from the column by washing with an IEC wash buffer (50 mM Tris, approximately 45 mM NaCl, pH approximately 7.4,), and AAT was subsequently eluted using IEC elution buffer (approximately 50 mM Tris, about 95 mM NaCl, pH approximately 7.4).

2.2.3 Hydrophobic Interaction Chromatography (HIC)

The eluate from the IEC column was prepared for HIC by adding ammonium sulfate to a final concentration of approximately 1 M. The solution was then filtered and applied to a hydrophobic interaction column (GE Healthcare Phenyl Sepharose high sub), which had been equilibrated with HIC Wash Buffer (50 mM Tris, 1 M Ammonium Sulfate, pH approximately 7.4). The column was loaded at approximately 40 grams protein/L gravity settled resin. During the load, AAT did not bind to the hydrophobic column matrix and flowed through the column. At the completion of the load, unbound AAT remaining in the packed column was washed off the column using HIC Wash Buffer. The combined column flow through and subsequent wash were concentrated by ultra-filtration and diafiltered into a phosphate buffer (40 mM sodium phosphate, pH approximately 7.4).

The product was found to be ≧96% pure AAT as determined by both SDS-Page and immunological assays such as ELISA or nephelometry, and was ≧93% monomer by size exclusion HPLC. The recovery based on the functionally active AAT content of the Cohn Fraction IV paste was 40 to 60% or approximately 20 to 40% of normal plasma content. On average, 89% of the purified AAT was active, while a range of 79-99% was typically observed.

TABLE 1

Purification of AAT according to example 2 (g Protein/L Plasma Yield)

| Experiment | pH/Ethanol Precipitation | | DTT/Aerosil | IEC Eluate | HIC Effluent | HIC Conc. | HIC Conc. Purity |
| --- | --- | --- | --- | --- | --- | --- | --- |
| | APO in Precipitate | AAT in Filtrate | Treated Filtrate | | | | |
| T070216 | 0.678 | 0.064* | 0.601 | 0.515 | 0.394 | 0.425 | 99.6% |
| T070226 | 0.757 | 0.589 | 0.575 | 0.405 | 0.368 | 0.274 | 99.7% |
| T070230 | 0.690 | 0.604 | 0.477 | 0.339 | 0.337 | 0.252 | 99.9% |

*AAT potency assay interference was sometimes observed at this step.

2.3 Further Purification of ApoA-I

Approximately 50 g of ApoA-I Precipitate obtained as described in 2.1 were suspended with a seven-fold amount of Tris-HCl, pH 8.0, buffer and stirred for approximately 2 h at room temperature. The suspension was then filtered through a cellulose filter coated with filter aid (Celite™ 574).

Solid ammonium sulphate was added to the ApoA-I containing filtrate to final concentrations of 0.8, 0.9, 1.0, 1.2 and 1.4 M. The pH of each suspension was adjusted to between 7.0 and 7.5. The suspensions were then incubated for at least 2 h at room temperature before the precipitates were finally separated by filtration through a cellulose filter coated with Celite™ 574 filter aid.

Using this method ApoA-I preparations of a purity of up to 89% were obtained which corresponds to pharmaceutical grade purity.

Example 3

Purification of ApoA-I and AAT Using Adsorption of ApoA-I to Fumed Silica 3.1 Separation of ApoA-I and AAT: Binding to Fumed Silica Fraction $IV_1$ paste was suspended in a suspension buffer (100 mM Tris, 20 mM NaCl, pH approximately 9.6) and stirred for approximately 2 hours at approximately 5° C. The amount of buffer utilized was approximately 12 kg's per kg of the plasma-containing fraction (Fraction IV$_1$). To maximize AAT yield, the Tris buffer suspension was heated to approximately 43° C. for a period of approximately 1.5 hours, then cooled to approximately 5° C.

The Tris buffer suspension was then treated with DTT and fumed silica (Aerosil™ 380). DTT was added to the Tris buffer suspension at a concentration of about 30 mM. The solution was stirred for approximately 2 hours at approximately 5° C. at a pH around 9.4. The pH of the DTT-treated extract was then adjusted to about 7.8 using a dilute hydrochloric acid solution. The fumed silica (Aerosil™ 380) was then added at approximately 16.7 grams/Liter plasma equivalent in the plasma containing paste fraction. The suspension was stirred for approximately 1 hour at approximately 5° C. at pH 7.5 to 8.0. Celpure™ C1000 filter aid was added at a ratio of 3 parts filter aid to one part silica, by weight, and the mixture was stirred for 15 minutes. The soluble AAT fraction was separated from the precipitated fumed silica/ApoA-I, and contaminating proteins using a filter press, yielding the AAT final filtrate. The AAT filtrate was processed further while the fumed silica APO A-1 precipitate was collected for further purification.

3.2 Further Purification of AAT:

AAT was further purified by ion exchange chromatography and hydrophobic interaction chromatography as described in 2.2.2 and 2.2.3.

Example 4

Purification of ApoA-I and AAT by Ion Exchange Chromatography and Hydrophobic Interaction Chromatography 4.1 Separation of ApoA-I and AAT The Fraction IV$_1$ paste was suspended in a suspension buffer (100 mM Tris, 20 mM NaCl, pH approximately 9.6) and stirred for 2 hours at approximately 5° C. The amount of buffer utilized was approximately 12 kg's per kg of the plasma-containing fraction (Fraction IV$_1$). The Tris buffer suspension was heated to approximately 43° C. for a period of around 1.5 hours, then cooled to approximately 5° C.

The Tris buffer suspension was then treated with DTT and fumed silica (Aerosil™ 380). DTT was added to the Tris buffer suspension at a concentration of 30 mM. The solution was stirred for 2 hours at approximately 5° C. at a pH of approximately 9.4. The fumed silica (Aerosil™ 380) was then added at approximately 16.7 grams/Liter plasma equivalent in the plasma containing paste fraction. The suspension was stirred for approximately 1 hour at around 5° C., while maintaining a pH of approximately 9.4. Celpure™ C1000 filter aid was added at a ratio of 3 parts filter aid to one part fumed silica, by weight, and the mixture was stirred for about 15 minutes. The soluble AAT/ApoA-I fraction was separated

TABLE 2

Purification of AAT according to example 3

| | | DTT/Aerosil Step | | | | HIC Concentrate | | |
| --- | --- | --- | --- | --- | --- | --- | --- | --- |
| Run | Condition | APO in Cake (g/L) | APO in Filtrate (g/L) | AAT in Filtrate (g/L) | IEC Eluate (g/L) | HIC Effluent (g/L) | AAT Yield (g/L) | SDS-Page |
| T070228 | absorption at pH 7.8; Heated Extract | NT | 0.06 | 0.472 | 0.568 | 0.579 | 0.461 | 100% |
| T070229 | Absorption at pH 7.8; Extract Not Heated | 0.596 | ND | 0.395 | 0.541 | 0.468 | 0.358 | 99.6% |
| T070232 | Absorption at pH 8.0; Heated Extract | NT | 0.280 | 0.774 | 0.775 | 0.589 | 0.432 | 99.8% |
| T070233 | Absorption at pH 7.5; Extract Not Heated | NT | ND | 0.292 | 0.458 | 0.336 | 0.280 | 99.7% |
| T083017 | Absorption at PH 7.8; Extract Not Heated | 0.540 | 0.060 | 0.254 | 0.410 | 0.313 | 0.246 | 99.5% |

NT = Not Tested

The product was ≧96% pure AAT as determined by both SDS-Page and immunological assays and is ≧93% monomer by size exclusion HPLC. The recovery based on the functionally active AAT content of the Cohn Fraction IV paste was 40 to 60% or approximately 20 to 40% of normal plasma content. On average, 89% of the purified AAT was active, while a range of 79-99% was typically observed.

3.3 Further Purification of ApoA-I

ApoA-I was released from the fumed silica by resuspending the fumed silica separated from AAT in step 3.1 in 50-100 mM Tris buffer at pH 9.5. After subsequent separation from the fumed silica by centrifugation or filtration ApoA-I may be further purified as described in 2.3.

from the precipitated fumed silica/contaminating proteins using a filter press, yielding the AAT/ApoA-I final filtrate.

AAT and ApoA-I were further purified by ion exchange chromatography and hydrophobic interaction chromatography as described in 2.3.2 and 2.3.3, except that during the hydrophobic interaction chromatography step, ApoA-I was eluted after the AAT wash step with water.

The AAT combined column flow through and subsequent wash were concentrated by ultra-filtration and diafiltered into a phosphate buffer (40 mM sodium phosphate, pH approximately 7.4. The product was ≧96% pure AAT as determined by both SDS-Page and immunological assays, and was ≧93% monomer by size exclusion HPLC. The recovery based on the functionally active AAT content of the Cohn Fraction IV paste was 40 to 60% or approximately 20 to 40% of normal plasma content. On average, 89% of the purified AAT was active, while a range of 79-99% was typically observed.

4.2 Further Processing of AAT

TABLE 3

Average process yields from each step with 50 kg Fraction IV$_1$ as starting material

|  | Fraction IV-1 Extract (g/L Plasma) | AAT/APO A-1 Filtrate (g/L Plasma) | IEC Eluate (g/L Plasma) | HIC Effluent (g/L plasma) | HIC WFI Wash (g/L Plasma) | HIC Concentrate (g/L Plasma) |
|---|---|---|---|---|---|---|
| AAT | 0.71 | 0.562 | 0.556 | 0.450 | N/A | 0.450 |
| APO A-1 | 0.70 | 0.466 | 0.340 | None Det. | 0.387 | None. Det |

Example 5

Purification of ApoA-I and AAT by Negative Mode Ion-Exchange Chromatography Followed by Hydrophobic Interaction Chromatography 5.1 Purification with DTT and Silica Extraction of the Fraction IV-1 and purification with DTT and silica were performed as described in example 4.1.

5.2. Ion Exchange Chromatography

The AAT/ApoA-I final filtrate was adjusted to a pH range of about 7.4 by the addition of a dilute hydrochloric acid solution. The conductivity of the AAT/ApoA-I filtrate was adjusted to approximately 15 mS/cm at 22.0° C. by the addition of a 2 M NaCl solution. The pH/conductivity adjusted AAT/ApoA-I final filtrate was applied directly onto a chromatography column containing the anion exchange resin EMD TMAE Fractogel 650 (m) equilibrated with an equilibration buffer (50 mM Tris, pH 7.4, 15 mS/cm conductivity). Contaminating proteins were bound to the column while AAT and ApoA-I flowed through during the load. The AAT/ApoA-I containing ionic exchange column flow through fraction was processed further as indicated.

5.3. Separation of ApoA-I and AAT: Hydrophobic Interaction Chromatography

The AAT/ApoA-I IEC flow through was prepared for HIC by adding ammonium sulfate to a final concentration of 1 M. This solution was then filtered and applied to a hydrophobic interaction chromatography column (GE Healthcare Phenyl Sepharose high sub) that was equilibrated in an HIC wash buffer (50 mM Tris, pH 7.4, 1M Ammonium Sulfate). Initial elution during the load provided an AAT-containing effluent, and elution with additional wash buffer (50 mM Tris, pH 7.4, 1 M ammonium sulfate) removed any AAT retained in the column. The combined effluent and washes were concentrated by ultrafiltration and diafiltered into a phosphate buffer. Once the AAT fraction was removed, additional impurities were washed off the column with a 0.1 to 0.2 M ammonium sulfate solution, and then the ApoA-I was eluted from the column using water.

TABLE 4

Average yields of 6 runs according to example 5

|  | Fraction IV-1 Extract | Fraction IV-1 Filtrate | IEC Flow Through | HIC Effluent | HIC WFI Wash | HIC Concentrate |
|---|---|---|---|---|---|---|
| AAT Yield (g/L Plasma) | 0.715 | 0.691 | 0.505 | 0.116* | N/A | 0.415 |
| APO A-1 Yield (g/L Plasma) | 0.758 | 0.715 | 0.636 | 0 | 0.572 | 0 |

*AAT Potency interference at the HIC Effluent.

N/A = not applicable as AAT is present in fraction, but the wash with "water for injection" (WFI) is a waste fraction and AAT is not recovered from it.

The product was ≥96% pure AAT as determined by both SDS-Page and immunological assays and was ≥93% monomer by size exclusion HPLC. The recovery based on the functionally active AAT content of the Cohn Fraction IV paste was 40 to 60% or approximately 20 to 40% of normal plasma content. On average, 89% of the purified AAT was active, while in 6 runs, a range of 79-99% was observed.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

It is to be understood that various alterations or additions may be made to the parts previously described without departing from the spirit or ambit of the present invention.

The invention claimed is:

1. A method for purifying Apolipoprotein A-I (ApoA-1) and Alpha-1-Antitrypsin (AAT) from a single starting human plasma fraction containing both proteins comprising:

i) treating a starting human plasma fraction comprising ApoA-1 and AAT to separate an ApoA-1 containing fraction from an AAT containing fraction, comprising
   a) treating the starting human plasma fraction which is used as the starting material such that both ApoA-1 and AAT are solubilized;
   b) precipitating the solubilized ApoA-1 by adding ethanol to a concentration of 8-14% v/v and adjusting the pH to about 5 to about 6 so that ApoA-1 precipitates and AAT remains in solution; and
   c) separating precipitated ApoA-1 from the solution containing AAT; and
ii) separately purifying ApoA-1 and AAT in one or more processing steps.

2. The method according to claim 1, wherein the starting human plasma fraction is selected from one or more of Cohn fractions IV, precipitates from Kistler-Nitschmann supernatants A and A+1, and ammonium sulfate precipitates.

3. The method according to claim 2, wherein the one or more Cohn fractions IV is Cohn fraction $IV_1$.

4. The method according to claim 1, wherein AAT and ApoA-1 are not exposed to a pH of 13.69 or above.

5. The method according to claim 1, wherein AAT and ApoA-1 are not exposed to a pH of 13 or above.

6. The method according to claim 1, wherein AAT and ApoA-1 are not exposed to a pfd of 12 or above.

7. The method according to claim 1, wherein AAT and ApoA-1 are not exposed to a pH of 11 or above.

8. The method according to claim 1, wherein the starting human plasma fraction is solubilized at step a) in a buffer comprising about 50-150 mM Tris and about 0-20 mM NaCl at a pH of about 8.0 to 10.0.

9. The method according to claim 1, wherein ApoA-1 is precipitated at a temperature at or below 10° C.

10. A method according to claim 1, further comprising a viral reduction step.

11. The method according to claim 10, wherein the viral reduction step comprises pasteurization at about 60° C.

12. The method according to claim 11, wherein the pasteurization step is carried out on a solution comprising at least 40% w/w sucrose and at least 4% w/w potassium acetate.

13. The method according to claim 12, wherein the viral reduction step comprises filtration through a filter that can remove viral particles.

\* \* \* \* \*

UNITED STATES PATENT AND TRADEMARK OFFICE
CERTIFICATE OF CORRECTION

| | | |
|---|---|---|
| PATENT NO. | : 8,436,152 B2 | |
| APPLICATION NO. | : 12/673723 | |
| DATED | : May 7, 2013 | |
| INVENTOR(S) | : Nathan Brinkman et al. | |

It is certified that error appears in the above-identified patent and that said Letters Patent is hereby corrected as shown below:

Title Page, Item (75) Inventors: should read

--(75) Inventors:     Nathan Brinkman, Herscher, IL (US);
                              Douglas Bigler, Kankakee, IL (US);
                              Reinhard Bolli, Gümligen (CH);
                              Vreni Foertsch, Winznau (CH).--.

Signed and Sealed this
Eighth Day of April, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,436,152 B2 | Page 1 of 1 |
| APPLICATION NO. | : 12/673723 | |
| DATED | : May 7, 2013 | |
| INVENTOR(S) | : Nathan Brinkman et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 465 days.

Signed and Sealed this
Second Day of September, 2014

Michelle K. Lee
*Deputy Director of the United States Patent and Trademark Office*